US011646434B2

(12) United States Patent
Narayan et al.

(10) Patent No.: US 11,646,434 B2
(45) Date of Patent: May 9, 2023

(54) CROSSOVER RESISTANT MATERIALS FOR AQUEOUS ORGANIC REDOX FLOW BATTERIES

(71) Applicant: UNIVERSITY OF SOUTHERN CALIFORNIA, Los Angeles, CA (US)

(72) Inventors: Sri R. Narayan, Arcadia, CA (US); G. K. Surya Prakash, Hacienda Heights, CA (US); Archith Nirmalchandar, Los Angeles, CA (US); Advaith Murali, Los Angeles, CA (US); Bo Yang, Los Angeles, CA (US); Sankarganesh Krishnamoorthy, Los Angeles, CA (US); Lena Hoober-Burkhardt, Los Angeles, CA (US); Robert Aniszfeld, Los Angeles, CA (US)

(73) Assignee: University of Southern California, Los Angeles, CA (US)

( * ) Notice: Subject to any disclaimer, the term of this patent is extended or adjusted under 35 U.S.C. 154(b) by 162 days.

(21) Appl. No.: 16/980,549

(22) PCT Filed: Mar. 12, 2019

(86) PCT No.: PCT/US2019/021774
§ 371 (c)(1),
(2) Date: Sep. 14, 2020

(87) PCT Pub. No.: WO2019/178041
PCT Pub. Date: Sep. 19, 2019

(65) Prior Publication Data
US 2021/0005918 A1    Jan. 7, 2021

Related U.S. Application Data

(60) Provisional application No. 62/641,776, filed on Mar. 12, 2018.

(51) Int. Cl.
*H01M 8/18* (2006.01)
*C07C 309/32* (2006.01)

(52) U.S. Cl.
CPC ........... *H01M 8/188* (2013.01); *C07C 309/32* (2013.01)

(58) Field of Classification Search
CPC .......................... H01M 8/188; C07C 309/32
See application file for complete search history.

(56) References Cited

U.S. PATENT DOCUMENTS

| 2014/0370403 A1 | 12/2014 | Narayan | ............... | H01M 8/188 |
| | | | | 429/418 |
| 2015/0243991 A1 | 8/2015 | Huskinson | .......... | H01M 4/9008 |
| | | | | 429/105 |

(Continued)

FOREIGN PATENT DOCUMENTS

CN     105566884     *    5/2016

OTHER PUBLICATIONS

CN 105566884 MT (Year: 2016).*

(Continued)

*Primary Examiner* — Alexander Usyatinsky
(74) *Attorney, Agent, or Firm* — Brooks Kushman P.C.

(57) ABSTRACT

An organic flow battery having a positive electrode electrolyte containing organic compounds with extended conjugation and/or cyclic side chains is provided. The flow battery includes a positive electrode and a positive electrode electrolyte including first solvent and a first redox couple. The positive electrode electrolyte flows over and contacting the positive electrode. The first redox couple includes a first organic compound and a reduction product of the first organic compound. The flow battery also includes a negative electrode and a negative electrode electrolyte including a second solvent and a second redox couple. The negative (Continued)

electrode electrolyte flows g over and contacts the positive electrode. Typically, an ion exchange membrane is interposed between the positive electrode and the negative electrode Characteristically, the first organic compound resists crossover through the ion exchange membrane.

21 Claims, 13 Drawing Sheets

(56) References Cited

U.S. PATENT DOCUMENTS

2016/0260994 A1* 9/2016 Kong ................ C08J 5/2237
2016/0322662 A1 11/2016 Schmitz ............ H01M 8/1086
2017/0062863 A1* 3/2017 Huang ................ H01M 8/188
2017/0244127 A1* 8/2017 Tucker ................ H01M 4/94

OTHER PUBLICATIONS

Aubrey, M.L. et al., "A Dual-Ion Battery Cathode via Oxidative Insertion of Anions in a Metal-Organic Framework," J. Am. Chem. Soc. 137 (42), 2015, pp. A-I.

Wang, J. et al., "Investigation on redox mechanism of p-aminophenol in non-aqueous media by FT-IR spectroelectrochemistry," Electrochimica Acta 91 (2013), pp. 152-157.

Wedege, K. et al., "Organic Redox Species in Aqueous Flow Batteries: Redox Potentials, Chemical Stability and Solubility," Scientific Reports, 6:39101, DOI:10.1038/srep39101, (2016, pp. 1-13.

International Search Report dated Jun. 24, 2019 for PCT/US2019/021774, 11 pgs.

* cited by examiner

Electrochemisty of BPS

Reversibility and positive electrode potential are very promising electrochemical properties

Electrochemistry of DMMHQ

"DMMHQ: 2,2'-methylenebis(benzene-1,4-diol)"

Unsulfonated  Sulfonated

Currents indicate 4-electron consistant with the structure of the molecule.

Electrochemistry of DMMS

"DMMS: 4,4'-methylenebis(2,5-dihydroxybenzenesulfonic acid).

Mixtures of sulfonated isomer

Currents indicate 4 electron reduction consitent with the structure

Electrochemisty of p-HQSU2 p-HQSU2  2,2'-sulfonybis(benzene-1,4-diol)

Diffusion Coefficients for Various Membranes Measured from Crossover Studies

| Memberane | Thickness, microns | Water Content, % | $D_{app}$, Apparent Diffusion Coefficient (cm²s⁻¹) | Normalized Diffusion Coefficient for thickness ($D_{app}$ * thickness in μm) |
|---|---|---|---|---|
| Nafion 117 | 175 | 30 | $3.12 \times 10^{-8}$ | $5.46 \times 10^{-4}$ |
| Fumatech F1850 | 50 | 17 | $1.66 \times 10^{-6}$ | $8.3 \times 10^{-5}$ |
| HPEEK E750 | 50 | <10 | $1.63 \times 10^{-7}$ | $8.15 \times 10^{-6}$ |

Fig. 8

| Material | Nafion | H-PEEK |
|---|---|---|
| pTSA | Yes | Not tested |
| DHDMBS | Yes | Yes |
| MMS | Yes | No, 300+ hours |
| HMS | Not tested | No, 200+ hours |
| BPS | Yes | No, 72+ hours |
| AQDS | No, long duration | No, long duration |

*Fig. 11*

CROSSOVER RESISTANT MATERIALS FOR AQUEOUS ORGANIC REDOX FLOW BATTERIES

CROSS-REFERENCE TO RELATED APPLICATIONS

This application is the U.S. national phase of PCT Appln. No. PCT/US2019/021774 filed Mar. 12, 2019, which claims the benefit of U.S. provisional application Ser. No. 62/641,776 filed Mar. 12, 2018, the disclosure of which is hereby incorporated in its entirety by reference herein.

TECHNICAL FIELD

In at least one aspect, the present invention is related to organic flow batteries with an advantageously diminished amount of crossover.

BACKGROUND

The integration of intermittent energy sources such as solar and wind energy into the electrical grid poses challenges in balancing the supply and demand. Such challenges can be addressed by employing rechargeable battery systems capable of storing large-scale electrical energy. These battery systems generally have high energy efficiency and are easily scalable. Amongst the existing electrochemical storage technologies, the redox flow battery is very promising system for grid scale energy storage. Unlike conventional battery systems, in the flow battery, the redox active material is stored in an external tank as solutions which can exist in both reduced or oxidized forms. The power is generated from a cell which is separated from the storage tanks, and can be connected, when needed. Pumps are employed to pass the electrolyte solutions through the cell. The cell typically contains three working components, 1) positive electrode (cathode) 2) negative electrode (anode) and 3) selective ion conducting polymer electrolyte membrane, separating the positive and negative electrolytes.

One of the principal problems affecting the durability and efficiency of redox flow batteries is the problem of crossover of molecules from the positive side of the cell to the negative side and vice versa. When crossover occurs, the cell voltage is reduced and the concentration of the materials is reduced.

Accordingly, there is a need for improved flow battery design with a decreased amount of crossover.

SUMMARY

In at least on aspect, the present invention solves one or more problems of the prior art by providing a redox flow battery that resists crossover from the positive side to the negative side. The flow battery includes a positive electrode and a positive electrode electrolyte including first solvent and a first redox couple. The positive electrode electrolyte flows over and contacts the positive electrode. The first redox couple includes a first organic compound and a reduction product of the first organic compound. The flow battery also includes a negative electrode and a negative electrode electrolyte including a second solvent and a second redox couple. The negative electrode electrolyte flows over and contacts the positive electrode. Typically, an ion exchange membrane is interposed between the positive electrode and the negative electrode. Characteristically, the first organic compound resists crossover through the ion exchange membrane.

In another aspect, the first solvent and the second solvent each independently include water.

In another aspect, the first organic compound and the second organic compound are dissolved in water and are capable of undergoing reversible redox reactions under various conditions of pH spanning from acidic to alkaline.

In another aspect, the first solvent and the second solvent are a mixture of water and organic solvents may be used.

In still another aspect, the flow batteries have the potential to meet the demanding requirements for grid-scale electrical energy storage. Other advantages of these battery systems are low cost, durability, environmentally benign and sustainability.

Aspects of the present invention relate to improvements that avoid crossover and thus achieve high durability and high energy efficiency: addressing the problem of crossover by tailoring the size of the molecules relative to the channels in the membrane; use of membranes with water content less than 40% to restrict the size of the hydrophilic domains that facilitate crossover; and use of molecule-membrane combinations where the acidity of the redox molecule is stronger than that the acid groups on the membrane. Specifically, the pKa values for the redox molecule are smaller than the acid groups on the membrane.

In still another aspect, a flow battery that resists crossover from the positive side to the negative side. The flow battery includes a positive electrode a positive electrode electrolyte including water and a first redox couple. The positive electrode electrolyte flows over and contacts the positive electrode. The first redox couple includes a first organic compound and a reduction product of the first organic compound. The flow battery also includes a negative electrode and a negative electrode electrolyte including water and a second redox couple. The negative electrode electrolyte flows over and contacts the positive electrode and an ion exchange membrane interposed between the positive electrode and the negative electrode, wherein the ion exchange membrane impedes crossover therethrough.

BRIEF DESCRIPTION OF THE DRAWINGS

FIG. 8. Comparison the diffusion coefficient of redox active DHDMBS through various membranes and their water content.

FIG. 11. Crossover of various molecules of small size through NAFION and H-PEEK.

DETAILED DESCRIPTION

Figure 1:
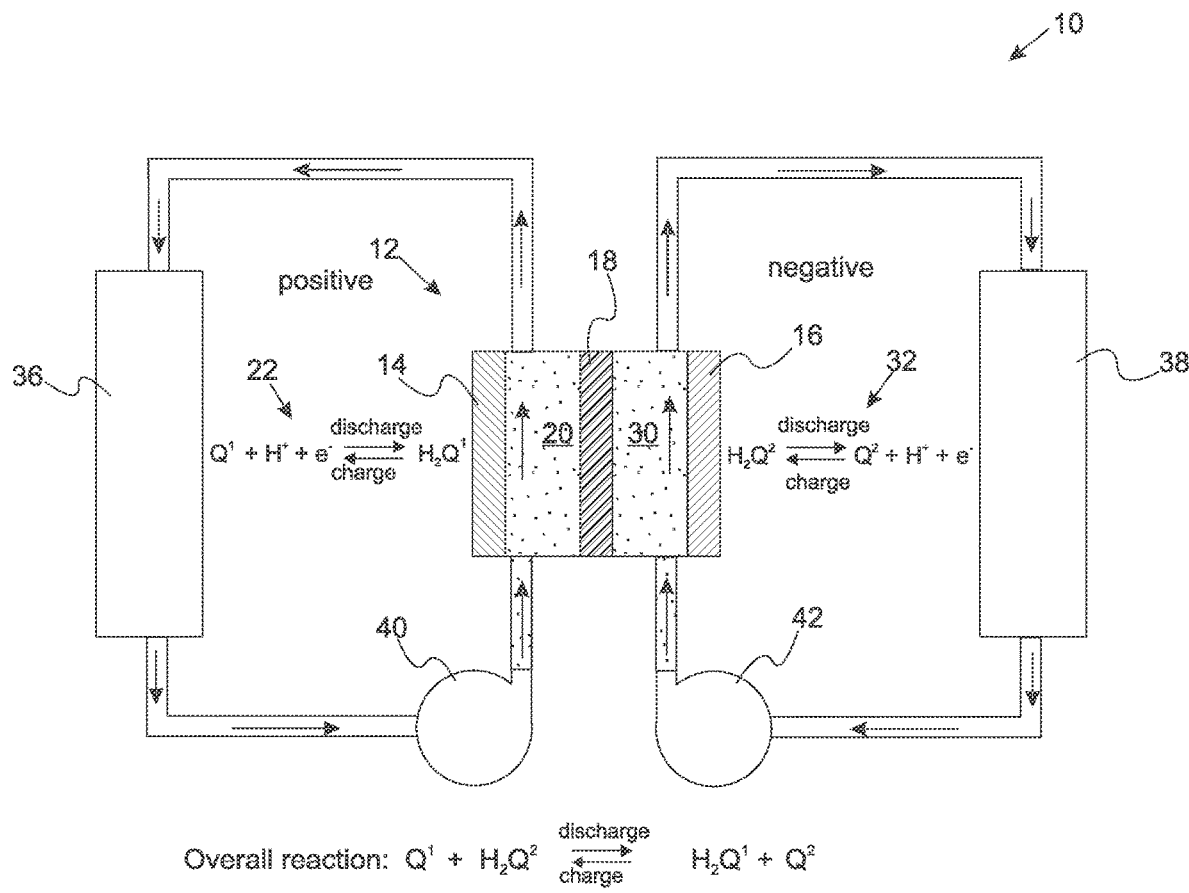
FIG. 1. A schematic of a flow battery system.

Reference will now be made in detail to presently preferred compositions, embodiments and methods of the present invention, which constitute the best modes of practicing the invention presently known to the inventors. The Figures are not necessarily to scale. However, it is to be understood that the disclosed embodiments are merely exemplary of the invention that may be embodied in various and alternative forms. Therefore, specific details disclosed herein are not to be interpreted as limiting, but merely as a representative basis for any aspect of the invention and/or as a representative basis for teaching one skilled in the art to variously employ the present invention.

Except in the examples, or where otherwise expressly indicated, all numerical quantities in this description indicating amounts of material or conditions of reaction and/or use are to be understood as modified by the word "about" in describing the broadest scope of the invention. Practice within the numerical limits stated is generally preferred. Also, unless expressly stated to the contrary: all R groups (e.g. $R_i$ where i is an integer or simply R) include alkyl, lower alkyl, $C_{1-6}$ alkyl, $C_{6-10}$ aryl, $C_{6-10}$ heteroaryl, $-NO_2$, $-NH_2$, $-N(R'R'')_2$, $-N(R'R''R''')_3{}^+L^-$, $-CF_3$, $-CCl_3$, $-CN$, $-SO_3H$, $-PO_3H_2$, $-COOH$, $-CO_2R'$, $-COR'$, $-CHO$, $-OH$, $-OR'$, $-O^-M^+$, $-SO3^-M^+$, $-PO3^-M^+$, $-COO^-M^+$, $-CF_2H$, $-CF_2R'$, $-CFH3$, and $-CFR'R''$ where R', R" and R''' are $C_{1-10}$ alkyl or $C_{6-18}$ aryl groups; single letters (e.g., "n" or "o") are 1, 2, 3, 4, or 5; percent, "parts of," and ratio values are by weight; the term "polymer" includes "oligomer," "copolymer," "terpolymer," and the like; molecular weights provided for any polymers refers to weight average molecular weight unless otherwise indicated; the description of a group or class of materials as suitable or preferred for a given purpose in connection with the invention implies that mixtures of any two or more of the members of the group or class are equally suitable or preferred; description of constituents in chemical terms refers to the constituents at the time of addition to any combination specified in the description, and does not necessarily preclude chemical interactions among the constituents of a mixture once mixed; the first definition of an acronym or other abbreviation applies to all subsequent uses herein of the same abbreviation and applies mutatis mutandis to normal grammatical variations of the initially defined abbreviation; and, unless expressly stated to the contrary, measurement of a property is determined by the same technique as previously or later referenced for the same property.

It is also to be understood that this invention is not limited to the specific embodiments and methods described below, as specific components and/or conditions may, of course, vary. Furthermore, the terminology used herein is used only for the purpose of describing particular embodiments of the present invention and is not intended to be limiting in any way.

It must also be noted that, as used in the specification and the appended claims, the singular form "a," "an," and "the" comprise plural referents unless the context clearly indicates otherwise. For example, reference to a component in the singular is intended to comprise a plurality of components.

The term "comprising" is synonymous with "including," "having," "containing," or "characterized by." These terms are inclusive and open-ended and do not exclude additional, unrecited elements or method steps.

The phrase "consisting of" excludes any element, step, or ingredient not specified in the claim. When this phrase appears in a clause of the body of a claim, rather than immediately following the preamble, it limits only the element set forth in that clause; other elements are not excluded from the claim as a whole.

The phrase "consisting essentially of" limits the scope of a claim to the specified materials or steps, plus those that do not materially affect the basic and novel characteristic(s) of the claimed subject matter.

With respect to the terms "comprising," "consisting of," and "consisting essentially of," where one of these three terms is used herein, the presently disclosed and claimed subject matter can include the use of either of the other two terms.

It should also be appreciated that integer ranges explicitly include all intervening integers. For example, the integer range 1-10 explicitly includes 1, 2, 3, 4, 5, 6, 7, 8, 9, and 10. Similarly, the range 1 to 100 includes 1, 2, 3, 4 . . . 97, 98, 99, 100.

Throughout this application, where publications are referenced, the disclosures of these publications in their entireties are hereby incorporated by reference into this application to more fully describe the state of the art to which this invention pertains.

As used herein "alkyl" refers to $C_{1-20}$ inclusive, linear (i.e., "straight-chain"), branched, saturated or at least partially and in some cases fully unsaturated (i.e., alkenyl and alkynyl) hydrocarbon chains, including for example, methyl, ethyl, propyl, isopropyl, butyl, isobutyl, tert-butyl, pentyl, hexyl, octyl, ethenyl, propenyl, butenyl, pentenyl, hexenyl, octenyl, butadienyl, propynyl, butynyl, pentynyl, hexynyl, heptynyl, and allenyl groups. "Branched" refers to an alkyl group in which a lower alkyl group, such as methyl, ethyl or propyl, is attached to a linear alkyl chain. "Lower alkyl" refers to an alkyl group having 1 to about 8 carbon atoms (i.e., a $C_{1-8}$ alkyl), e.g., 1, 2, 3, 4, 5, 6, 7, or 8 carbon atoms. "Higher alkyl" refers to an alkyl group having about 10 to about 20 carbon atoms, e.g., 10, 11, 12, 13, 14, 15, 16, 17, 18, 19, or 20 carbon atoms. The alkyl group can be optionally substituted (i.e., a "substituted alkyl") with another atom or functional group such as alkyl, substituted alkyl, halogen, aryl, substituted aryl, alkoxyl, hydroxyl, nitro, amino, alkylamino, dialkylamino, sulfate, mercapto, and the like. In the compounds below, lower alkyl is preferred.

As used herein "aryl" means a monovalent aromatic hydrocarbon having a single ring (i.e., phenyl) or fused rings (i.e., naphthalene). In a refinement, such aryl groups include from 6 to 12 carbon ring atoms. In another refinement, such aryl groups include 6 to 10 carbon ring atoms. Representative aryl groups include, by way of example, phenyl biphenyl, naphthyl, anthranyl, and naphthalene-1-yl, naphthalene-2-yl, and the like. The term "arylene" means a divalent aryl group.

As used herein "heteroaryl" means a monovalent aromatic group having a single ring or two fused rings and containing in the ring at least one heteroatom (typically 1 to 3 heteroatoms) selected from nitrogen, oxygen or sulfur. In a refinement, heteroaryl groups typically contain from 5 to 10 total ring atoms. In a refinement, heteroaryl groups have from 6 to 16 total ring atoms. In a refinement, the heteroaryl is a $C_{5-12}$ heteroaryl. Examples of heteroaryl include, but are not limited to, monovalent species of pyrrole, imidazole, thiazole, oxazole, furan, thiophene, triazole, pyrazole, isoxazole, isothiazole, pyridine, pyrazine, pyridazine, pyrimidine, triazine, indole, benzofuran, benzothiophene, benzimidazole, benzthiazole, quinoline, isoquinoline, quinazoline, quinoxaline and the like, where the point of attachment is at any available carbon or nitrogen ring atom. Additional examples of heteroaryl groups include, but are not limited to, furanyl, thienyl, and pridinyl group. The term "heteroarylene" means a divalent heteroaryl group.

Abbreviations:

"AQDS" means anthraquinone-2,7-disulfonic acid.

"BPS" means 4,4'-dihydroxy-[1,1'-biphenyl]-3,3'-disulfonic acid.

"DMDHMS" means 2,6-dimethyl-1,4-dihydroxybenzene-3-sulfonic acid.

"DMMHQ" means 2,2'-methylenebis(benzene-1,4-diol).

"DMMS" means 4,4'-methylenebis(2,5-dihydroxybenzenesulfonic acid).

"MMS" means 2,5-dihidroxy-4-methylbenzenesulfonic acid.

"MSE" means mercury/mercurous sulfate electrode.

"PEEK" means polyether ether ketone.

"RDE" means rotating disk electrode.

"TMBP" means 3,3',5,5'-tetramethyl-[1,1'-biphenyl]-4,4'-diol

"TMBPS" means 4,4'-dihydroxy-3,3',5,5'-tetramethyl-[1,1'-biphenyl]-2,2'-disulfonic acid.

With reference to FIG. 1, a schematic illustration of a flow battery that includes a pair of organic redox couples is provided. Flow battery 10 includes battery cell 12 which includes positive electrode 14, negative electrode 16, and polymer electrolyte membrane 18. In the context of a flow cell, reduction occurs during discharge at the positive electrode and oxidation occurs during discharge at the negative electrode. Conversely, oxidation occurs during charging at the positive electrode and reduction occurs during charging at the negative electrode. Polymer electrolyte membrane 18 (e.g., an ion exchange membrane) is interposed between positive electrode 14 and negative electrode 16. Positive electrode electrolyte 20 includes water and a first redox couple 22. In FIG. 1, a first redox couple 22 is depicted as an example. Positive electrode electrolyte 20 flows over and contacts positive electrode 14. First redox couple 22 includes a first organic compound $Q^1$ and a reduction product $H_2Q^1$ of the first organic compound. During discharge of the flow battery, the first organic compound $Q^1$ is reduced to the first reduction product $H_2Q^1$ of the first organic compound. During charging of the flow battery, the first reduction product $H_2Q^1$ is oxidized to the first organic compound $Q^1$. Negative electrode electrolyte 30 includes water and a second redox couple 32.

Negative electrode electrolyte 30 flows over and contacts the negative electrode 16. The second redox couple 32 can include a second organic compound $Q^2$ and a reduction product $H_2Q^2$ of the second organic compound. Alternatively, second redox couple 32 can include an inorganic compound. During discharge, the reduction product $H_2Q^2$ is oxidized to the second organic compound $Q^2$. In a refinement, the first organic compound has a standard electrode potential that is at least 0.3 volts higher than a standard electrode potential (e.g., MSE) for the second organic compound. In a refinement, compounds having a standard electrode potential that is at least 0.1 V positive to the MSE are suitable for the positive electrode electrolyte while compounds having a standard electrode potential that is at least 0.1 V negative to MSE are suitable for the negative electrode electrolyte. In another refinement, compounds having a standard electrode potential that is at least 0.3 V positive to the MSE are suitable for the positive electrode electrolyte while compounds having a standard electrode potential that is at least 0.3 V negative to MSE are suitable for the negative electrode electrolyte. Typical operation of the electrolytes is with a solution concentration from 0.1M to 5M, solution temperature from 10° C. to 90° C., and pH greater than or equal to 0 and less than or equal to 14 (e.g., pH 1 to 13).

Still referring to FIG. 1, flow battery 10 further includes a positive electrode reservoir 36 in fluid communication with the positive electrode 14. The positive electrode electrolyte 20 is stored in the positive electrode reservoir 36 to charge and discharge the flow battery. The positive electrode electrolyte 20 cycles through battery cell 12 from positive electrode reservoir 36 via the pumping action of pump 40. A negative electrode reservoir 38 is in fluid communication with the negative electrode 16. The negative electrode electrolyte 30 is stored in the negative electrode reservoir 38 to charge and discharge the flow battery. The negative electrode electrolyte 30 cycles through battery cell 12 from negative electrode reservoir 38 via the pumping action of pump 42.

The organic compounds set forth below can be used for either the first organic compound or the second organic compound. However, these compounds are most advantageously used for the first organic compound. In general, the compounds set forth herein resist crossover from the positive to the negative side.

In an embodiment, first organic compound $Q^1$ and/or second organic compound $Q^2$ are redox molecules with extended conjugated systems. In this regard, extended conjugation mean that pi (π) system that extends beyond and is larger than a phenyl group. Typically, the extended pi system includes additional pi bonds in groups of 2 or 3 π bonds. Therefore, an extended π system will include from 5 to 12 or more π bonds. Biphenols are a class of redox active molecules that has also been studied in great detail but their redox properties have never been applied to the field of organic redox flow batteries. Biphenols are 2 electron redox systems. An example of the redox chemistry of biphenol sulfonic acid (BPS) is as follows:

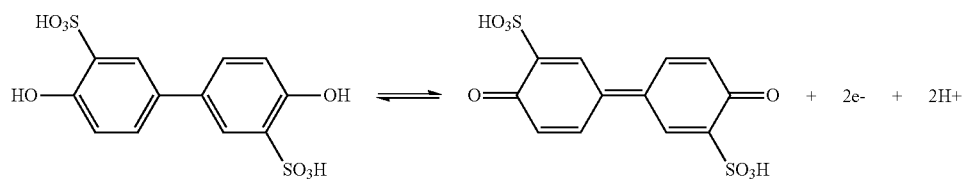

BPS
1

Figure 2A:
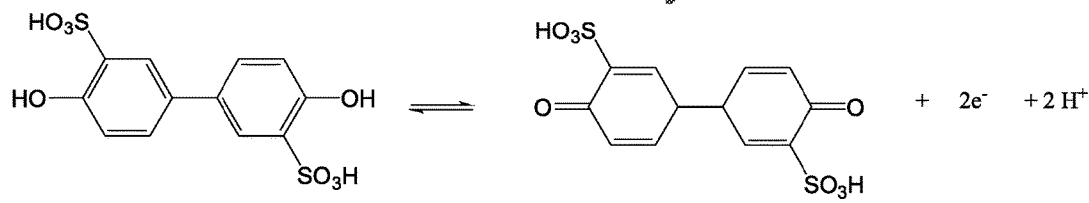
FIGS. 2A and 2B. Electrochemical Properties of Biphenol sulfonic acid.
Figure 2A:
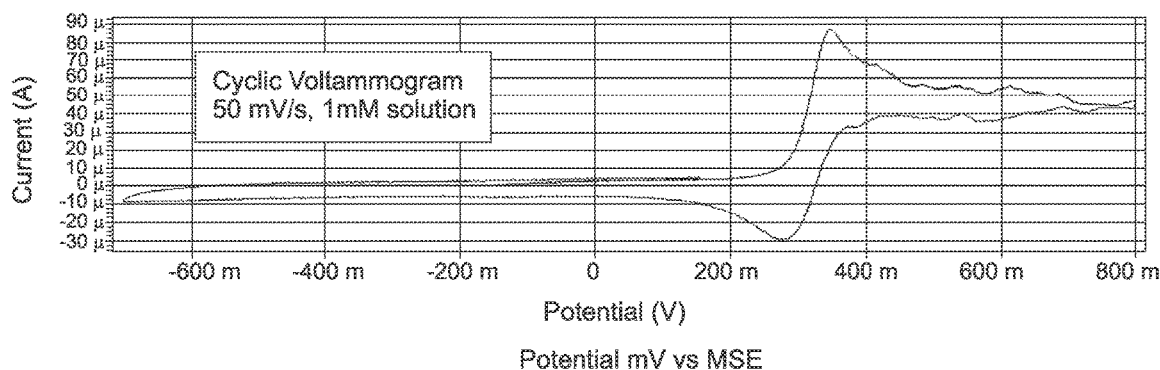
Figure 2B:
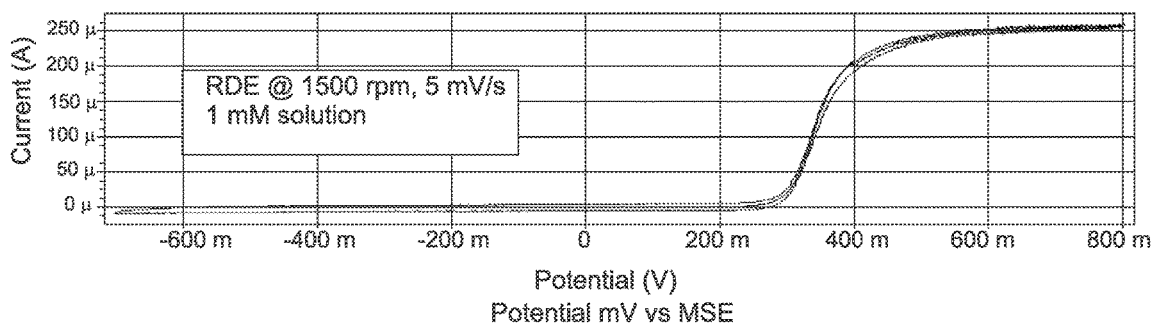

Biphenols have an extended conjugation unlike the quinone molecules that have been used before in organic redox flow batteries. These molecules are also readily sulfonated. The electrochemistry of biphenol sulfonic acid using cyclic voltammetry and rotating disk voltammetry shows that the charge-transfer kinetics is fast and the redox properties of this molecule are highly suitable for use in organic redox flow batteries (FIGS. 2A and 2B).

The biphenol molecule is an example of this class of molecules with extended conjugation and also have desirable electrochemical properties. Therefore, variations of the present invention are not only limited to the biphenolic compounds but is general to any molecule which has an extended conjugation capable of undergoing redox transformations. The extended conjugation of these molecules are also of larger size when compared to the one ring quinone system molecules, thus these molecules will also be crossover resistant. Examples of such redox active molecules with substituents that are enhanced in molecular size with extended conjugation is provided by formulae 2-5:

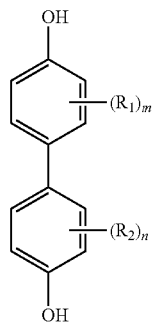

2

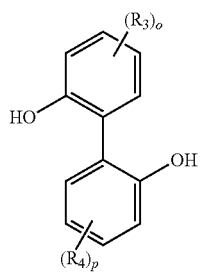

3

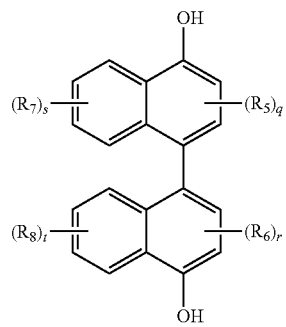

4

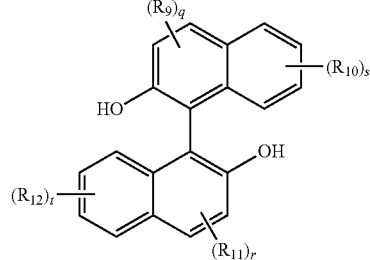

5 where in m, n, o, p are each independently 0, 1, 2, 3, or 4; q and r are each independently 0, 1, or 2; s and t are each independently 0, 1, 3, or 4; $R_1$, $R_2$, $R_3$, $R_4$, $R_5$, $R_6$, $R_7$, $R_8$, $R_9$, $R_{10}$, $R_{11}$ and $R_{12}$ are each independently —H, —R', —$NO_2$, —$NH_2$, —N(R'R'')$_2$, —N(R'R''R''')$_3^+$L$^-$, —$CF_3$, —$CCl_3$, —CN, —$SO_3H$, —$PO_3H_2$, —COOH, —$CO_2$R', —COR', —CHO, —OH, —OR', —O$^-$M$^+$, —$SO_3^-$M$^+$, —$PO_3^-$M$^+$, —COO$^-$M$^+$, —$CF_2$H, —$CF_2$R', —$CFH_3$ and —CFR'R'', where R', R'' and R''' are alkyl or aryl groups. L is any negatively charged counter ion (e.g., CL$^-$, Br$^-$, etc.). M is any positively charged counter ion (Na$^+$, K$^+$, etc.).

Figure 3:
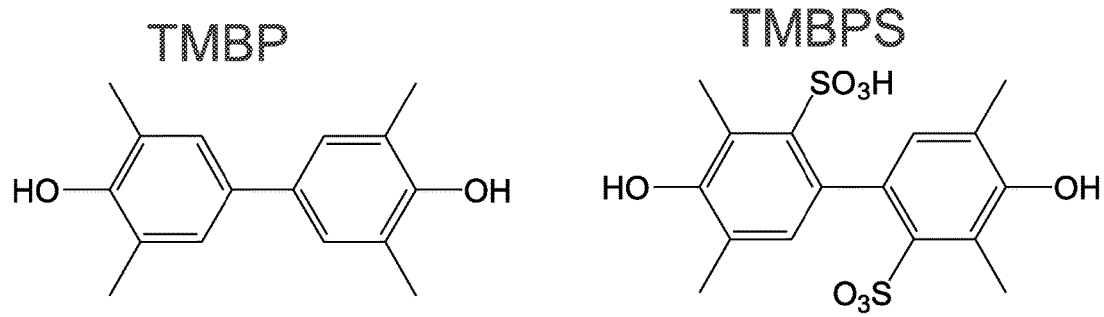
FIG. 3. Electrochemistry of TMBP and TMBPS.
Figure 3:
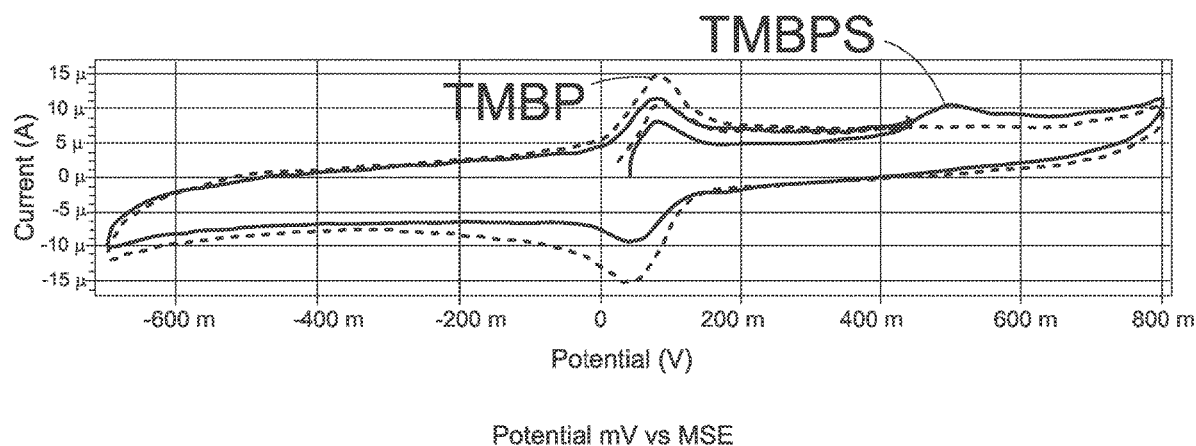
Figure 4A:
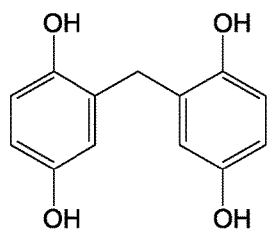
FIGS. 4A and 4B. Electrochemistry of DMMHQ: 2,2'-methylene bis(benzene-1,4-diol)
Figure 4A:
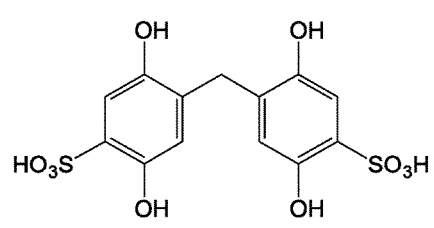
Figure 4A:
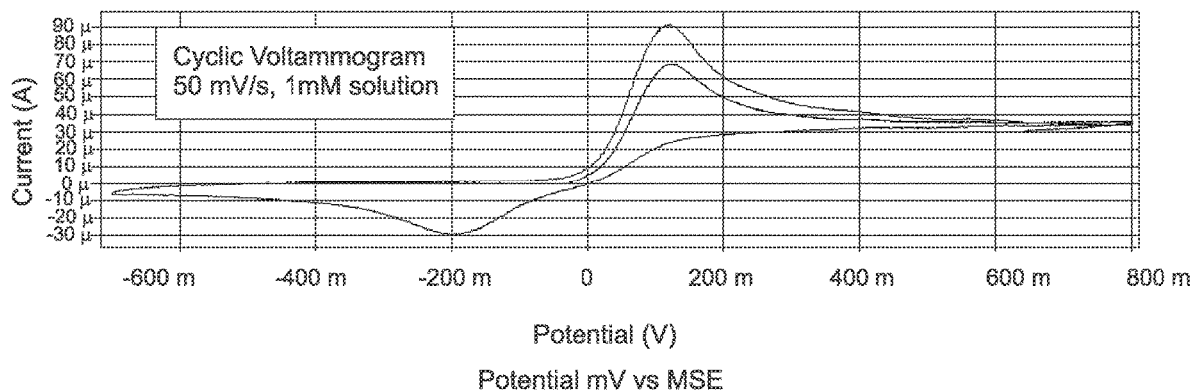
Figure 4B:
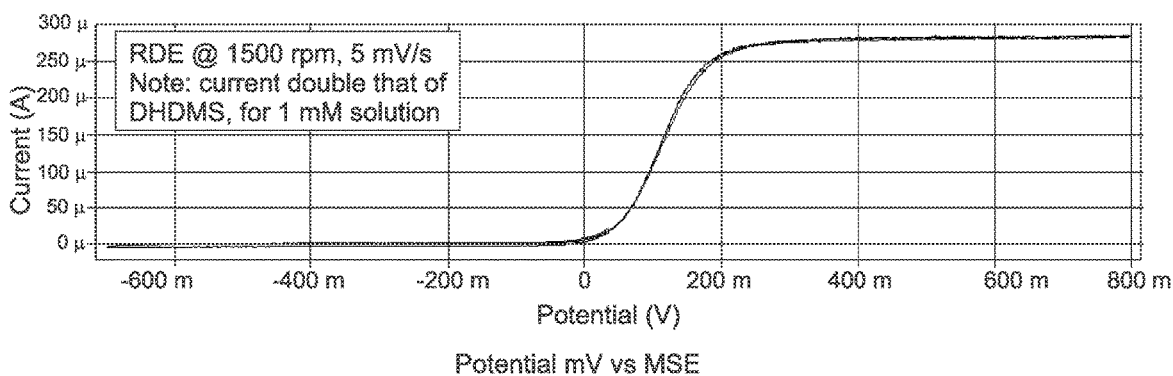
Figure 5A:
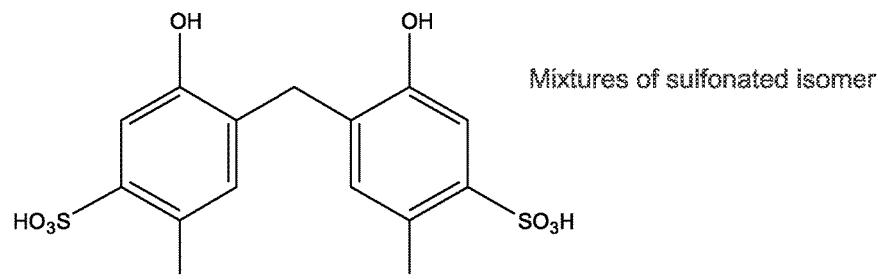
FIGS. 5A and 5B. Electrochemistry of DMMS: 4,4'-methylenebis(2,5-dihydroxybenzenesulfonic acid).
Figure 5A:
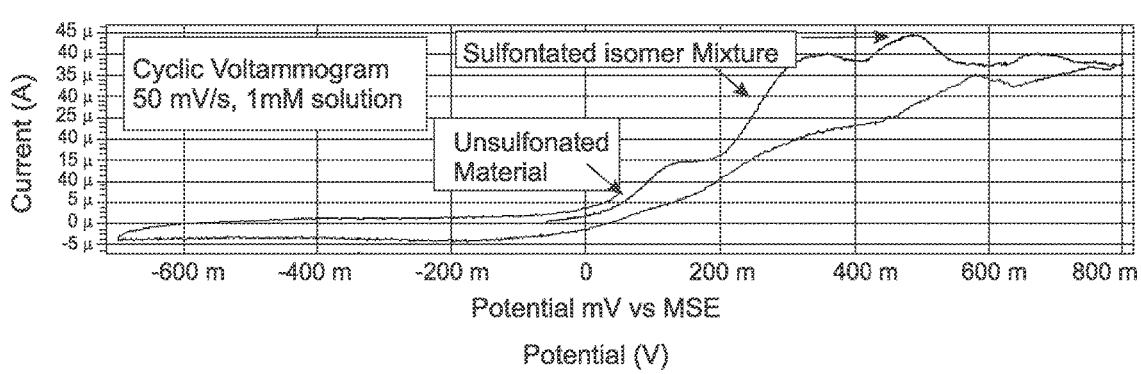
Figure 5B:
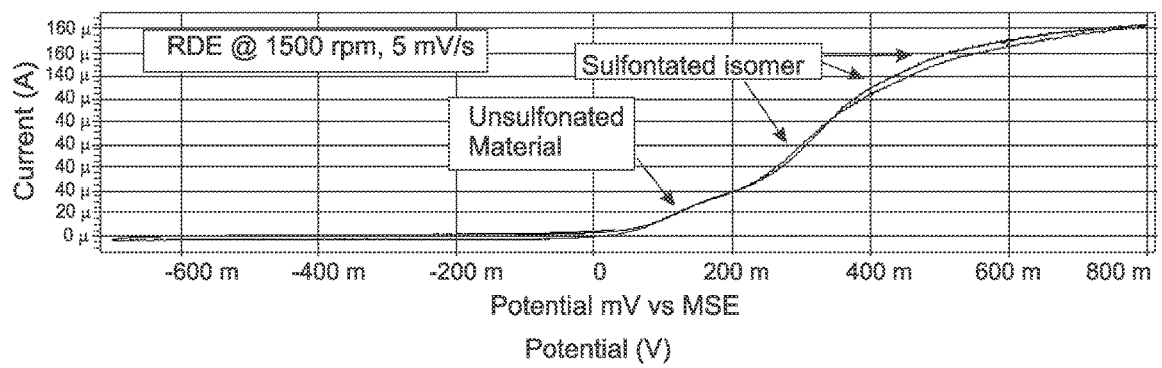
Figure 6A:
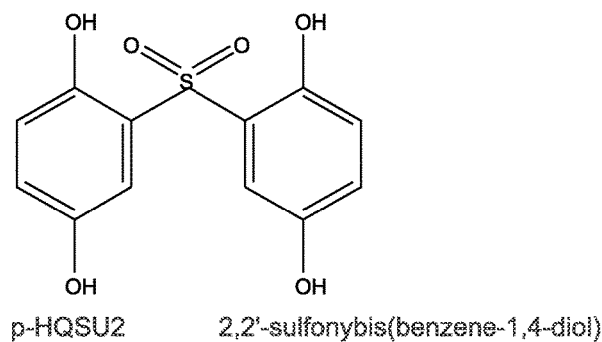
FIGS. 6A and 6B. Electrochemistry of p-HQSU2
Figure 6A:
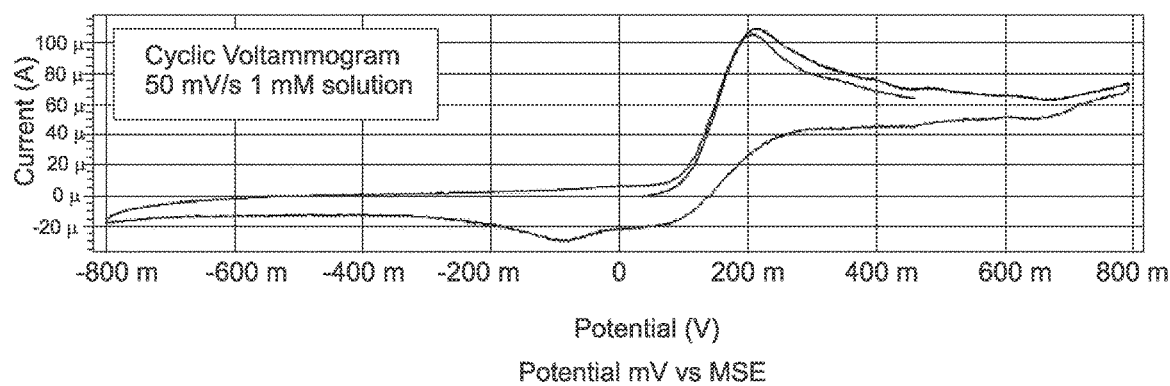
Figure 6B:
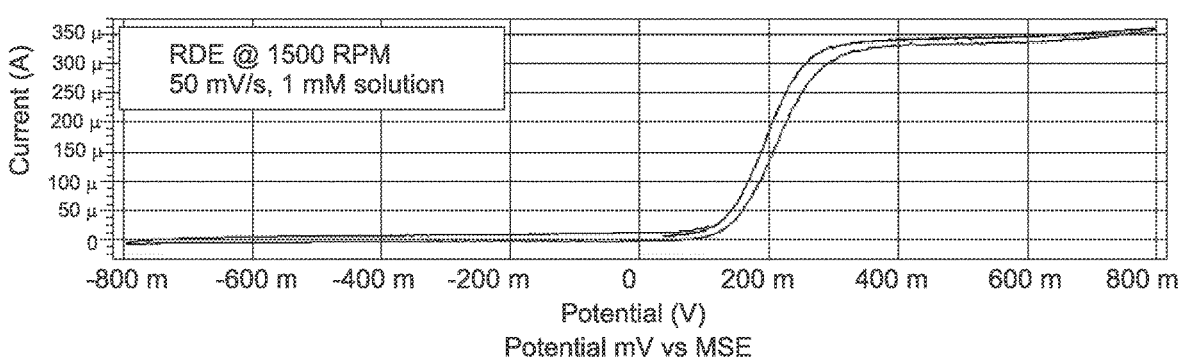

As an example of the class of substituted molecules with extended conjugation, it have been observed that the electrochemistry of the molecules TMBP and TMPBS are well suited from their electrochemical reversibility as determined by cyclic voltammetric studies (FIG. 3).

In another embodiment, the first and/or second organic compounds have cyclic side chains. Using cyclo-alkyl structures as substitutes on the redox system, the molecular size of the redox active molecules can be increased. These cyclo-alkyl groups are inactive towards redox chemistry and increase the size of the redox active molecule making them less likely to crossover across the membrane. Examples of such redox active molecules with substituents that are enhanced in molecular size with cyclic side chains are provided by Formulas 6 and 7:

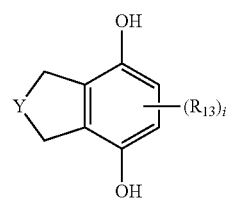

6

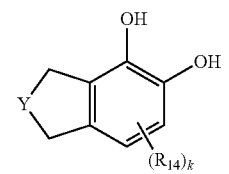

7 wherein i and k are each independently 0, 1, or 2; $R_{13}$ and $R_{14}$ are each independently —H, —R', —$NO_2$, —$NH_2$, —N(R'R'')$_2$, —N(R'R''R''')$_3^+$L$^-$, —$CF_3$, —$CCl_3$, —CN, —$SO_3H$, —$PO_3H_2$, —COOH, —$CO_2$R', —COR', —CHO, —OH, —OR', —O$^-$M$^+$, —$SO_3^-$M$^+$, —$PO_3^-$M$^+$, —COO$^-$M$^+$, —$CF_2$H, —$CF_2$R', —$CFH_3$ and —CFR'R'', where R', R'' and R''' are alkyl or aryl groups. Y is —(CH2)$_n$, —(CH2OCH2)$_n$, SO, $SO_2$, other substituted $C_{1-12}$ alkyl chains which may contain double bonds or triple bonds. L is any negatively charged counter ion (e.g., CL⁻, Br⁻, etc.). M is any positively charged counter ion (Na⁺, K⁺, etc.).

In another variation, redox active molecules are formed by linking two quinone containing moieties. Since small single ring redox active quinone molecules are prone to crossover, increasing their size by linking two moieties is a way to avoid crossover. Examples of this class of redox active molecules formed by linking two quinone containing moieties are provided by Formulas 8 and 9:

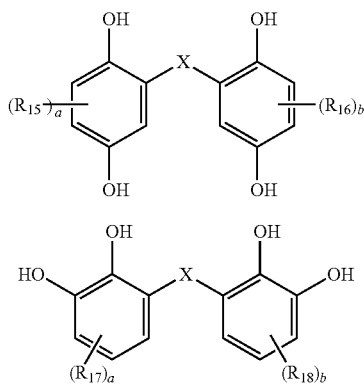

wherein a and b are each independently 0, 1, 2, or 3; $R_{15}$, $R_{16}$, $R_{17}$ and $R_{18}$ are each independently —H, —R', —NO$_2$, —NH$_2$, —N(R'R'')$_2$, —N(R'R''R''')$_3^+$L⁻, —CF$_3$, —CCl$_3$, —CN, —SO$_3$H, —PO$_3$H$_2$, —COOH, —CO$_2$R', —COR', —CHO, —OH, —OR', —O⁻M⁺, —SO$_3^-$M⁺, —PO$_3^-$M⁺, —COO⁻M⁺, —CF$_2$H, —CF$_2$R', —CFH$_3$ and —CFR'R'', where R', R'' and R''' are alkyl or aryl groups. X is —(CH$_2$)$_n$, —(CH$_2$OCH$_2$)$_n$, SO, SO$_2$, other substituted C$_{1-12}$ alkyl chains which may contain double bonds or triple bonds. L is any negatively charged counter ion. M is any positively charged counter ion. Examples of compounds having formula 8 and 9 have been shown to have good redox properties based on their cyclic voltammetric behavior and linear sweep voltammetry at the rotating disk electrode (FIGS. 4A, 4B, 5A, 5B, 6A and 6B). The currents indicate that four electrons can be transferred to each of these molecules.

In another embodiment, membranes with reduced crossover are provided. In this embodiment, the flow battery is of the general design of FIG. 1. Therefore, the flow battery 10 includes a positive electrode 14 and a positive electrode electrolyte 20 including water and a first redox couple 22. The positive electrode electrolyte 20 flows over and contacts the positive electrode 14. The first redox couple 22 includes a first organic compound Q¹ and a reduction product of the first organic compound H$_2$Q¹. The flow battery 10 also includes a negative electrode 16 and a negative electrode electrolyte 30 including water and a second redox couple. The negative electrode electrolyte 30 flows over and contacts the negative electrode 16 and an ion exchange membrane 18 interposed between the positive electrode 14 and the negative electrode 16. Characteristically, the ion exchange membrane 18 impedes crossover therethrough. In this regard, membranes with low water content will have smaller domains of water in the membrane and will not allow crossover of the molecules to occur. In a refinement, the water content is less than 40 weight percent of the total weight of the membrane with about 10 weight percent being optimal. This class of membranes is represented by membranes with acid equivalent weights greater than 1100 g/mole of protons. In a refinement, the membranes have acid equivalent weights greater than 1100 g/mole of protons less than 2500 g/mole of protons Examples of such membranes includes, but are not limited to, perfluorohydrocarbon membranes, sulfonated hydrocarbon membranes with an arene or substituted arene backbone such as sulfonated polyetherether ketone, sulfonated polyethersulfone, and polystyrenesulfonic acid-based membranes. Advantageously, the membranes of this embodiment, can be combined with the positive and negative electrolytes set forth above using the compounds. therein, in a variation, the first redox couple includes a first organic compound and a reduction product of the first organic compound such that the first organic compound resists crossover through the ion exchange membrane.

Figure 7:
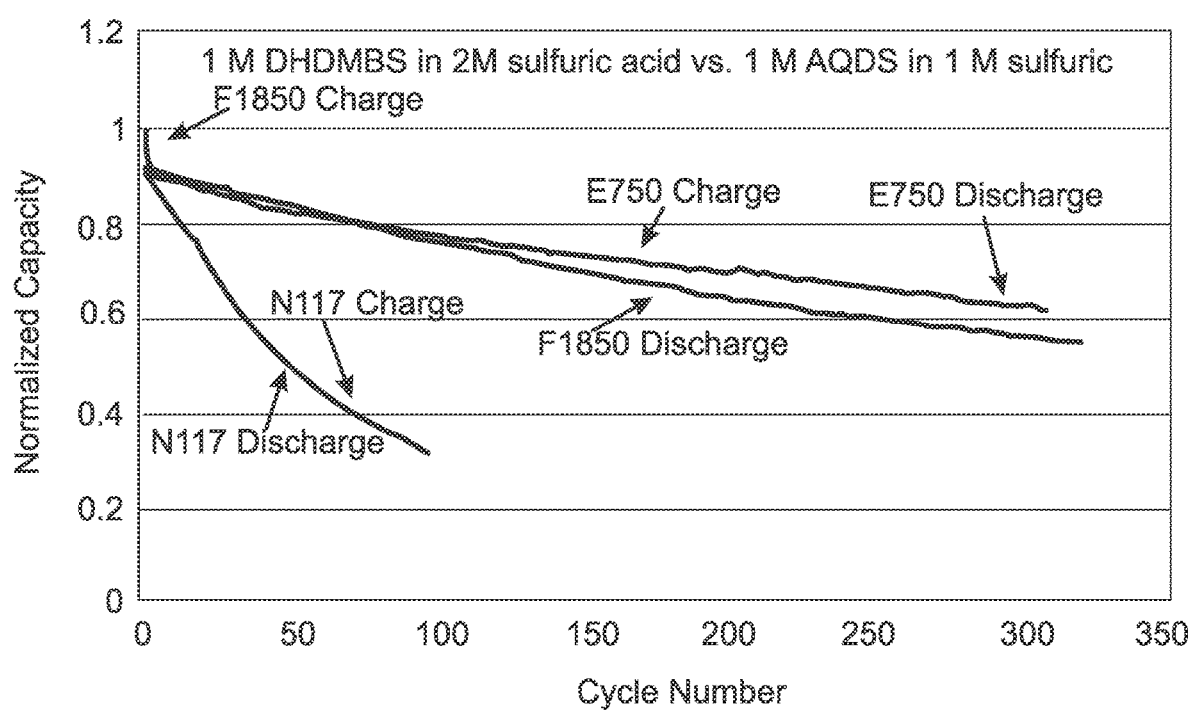
FIG. 7. Effect of Membrane type on the Capacity of DHDMBS/AQDS cell as a function of the cycling at 100 mA/cm$^2$.

The gradual reduction in capacity of dihydroxydimethylbenzoquinone sulfonic acid (DHDMBS) in a redox flow battery has been tested with the three different types of membranes. It is shown that the F1850 (perfluorohydrocarbon membrane with equivalent weight of 1850 g/mole of protons) and a sulfonated polyetheretherketone (H-PEEK) E750 membrane have significantly reduced fade rate compared to the NAFION 117 membrane with an equivalent weight of 1100 g/mole of protons (FIG. 7).

The diffusion coefficient of the redox active molecule through the three different types of membranes have been measured. FIG. 8 shows that the diffusion through the low water content membranes is lower than that of the membranes with high water content.

Figure 9:
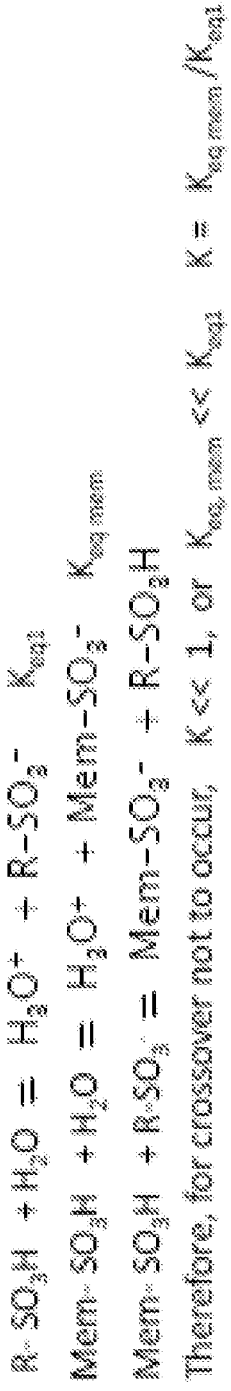
FIG. 9. Proton dissociation equilibria and its interaction with the proton dissociation equilibrium redox active molecule.
Figure 10:
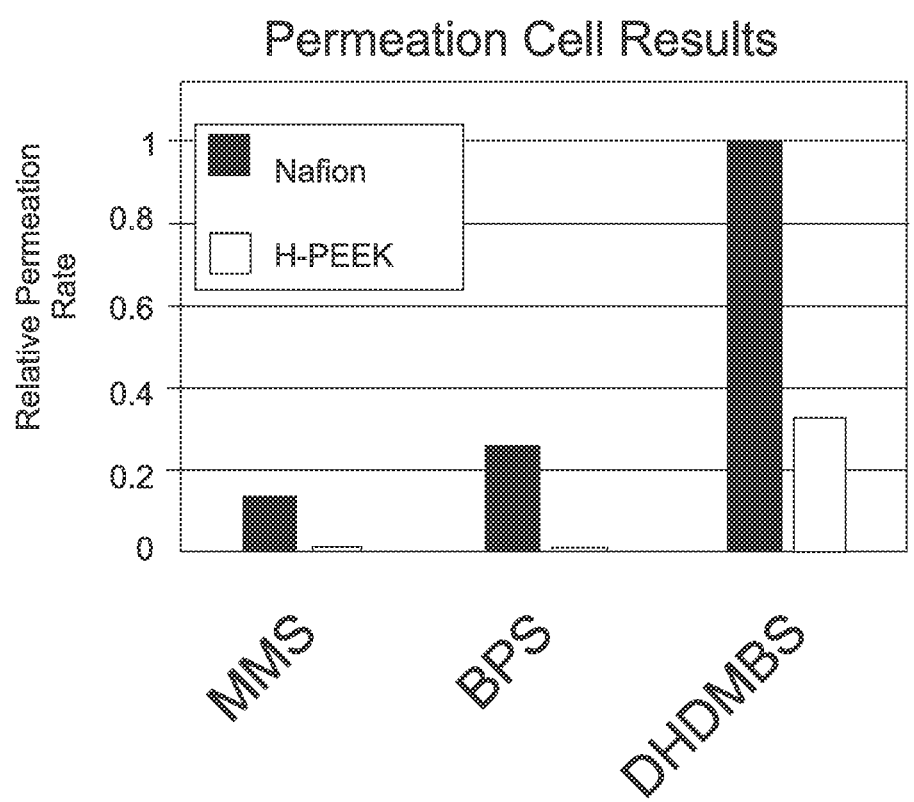
FIG. 10. Comparison of the permeation of MMS, BPS, and DHDMBS through H-PEEK and NAFION.

In another embodiment, molecules so chosen with the membrane combination where the acidity of the molecule is greater than that of the membrane will not crossover. When molecules are more acidic than the membrane, they will exist in the ionic form in the membrane. A cation exchange membrane with sulfonate groups will reject such a molecule. However, for this type of rejection to be effective, the acidity or the tendency of the acid membrane to dissociate and produce protons should be less than that of the redox active molecule that has the propensity to crossover. In effect, the pKa of the acid groups on the membrane is greater than that of the pKa of the redox active molecule. This method of rejection of molecules from the membrane ensures that even small molecules do not crossover. The principle of this action is described in FIG. 9. FIG. 10 provides comparison of the permeation of MMS, BPS, and DHDMBS through H-PEEK and NAFION.

This invention of molecule and membrane combination that prevents crossover is supported by the example data on crossover rates determined with NAFION and sulfonated PEEK membranes. Molecules such as MMS (2,5-dihidroxy-4-methylbenzenesulfonic acid) that are small crossover through NAFION, but do not crossover through H-PEEK. Whereas, DHDMBS is a weaker acid compared to H-PEEK and thus crosses over through H-PEEK. On the other hand, BPS is observed to crossover through NAFION, despite its larger size compared to DHDMBS and MMS.

The acidity of NAFION is higher than that of H-PEEK MMS is more acidic than H-PEEK but less acidic than NAFION. Thus, no crossover is observed with MMS through H-PEEK membranes (FIG. 11).

Figure 12:
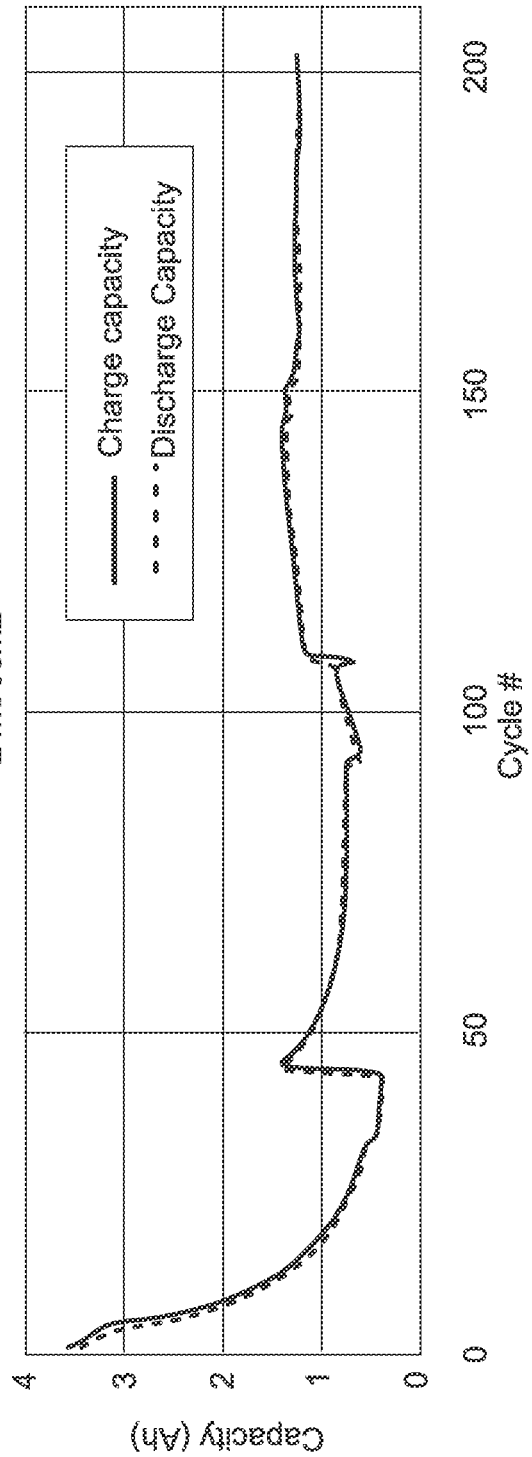
FIG. 12. Long term stable cycling showing lack of crossover related fade in a MMS/AQDS cell with a E750 H-PEEK membrane.
Figure 13:
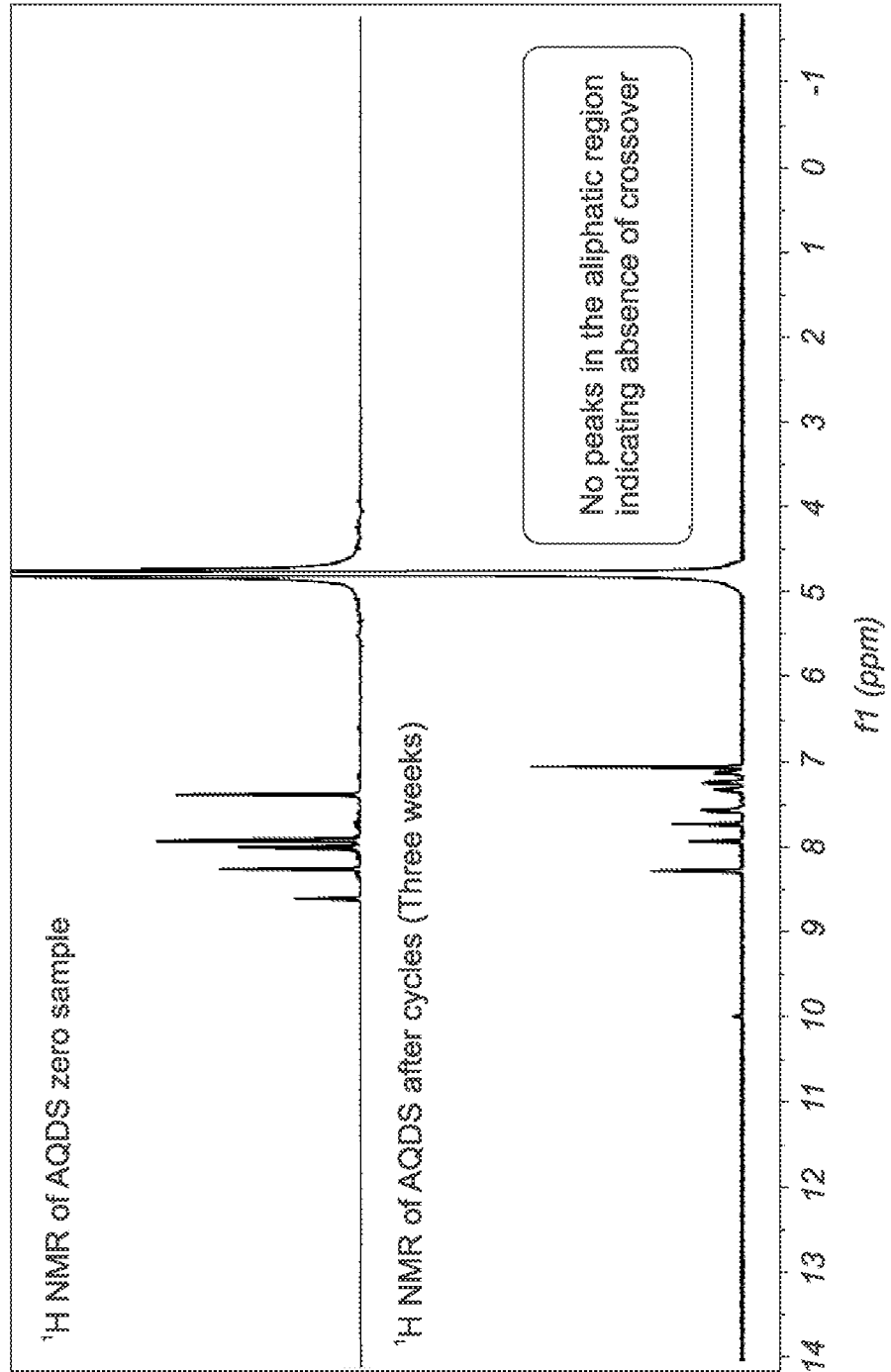
FIG. 13. NMR of MMS vs AQDS long term cycling showing lack of crossover.

FIG. 12 shows long term cycling of a MMS/AQDS cell with a E750 H-PEEK membrane showing lack of crossover related capacity fade due to the effective membrane-molecule combination. The NMR analysis of MMS vs AQDS shown in FIG. 13 shows no crossover over extended cycling.

While exemplary embodiments are described above, it is not intended that these embodiments describe all possible forms of the invention. Rather, the words used in the specification are words of description rather than limitation, and it is understood that various changes may be made without departing from the spirit and scope of the invention. Additionally, the features of various implementing embodiments may be combined to form further embodiments of the invention.

What is claimed is:

1. A flow battery comprising:
    a positive electrode;
    a positive electrode electrolyte including water and a first redox couple, the positive electrode electrolyte flowing over and contacting the positive electrode, the first redox couple including a first organic compound $Q^1$ and a reduction product $H_2Q_1$ of the first organic compound,
    a negative electrode;
    a negative electrode electrolyte including water and a second redox couple, the negative electrode electrolyte flowing over and contacting the positive electrode; and
    an ion exchange membrane interposed between the positive electrode and the negative electrode, wherein the first organic compound resists crossover through the ion exchange membrane and wherein the first organic compound has formulae 2, 3, 4, or 5:

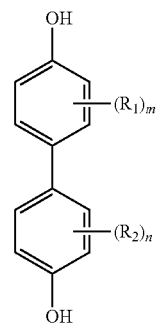

2

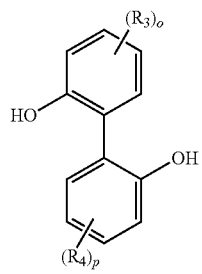

3

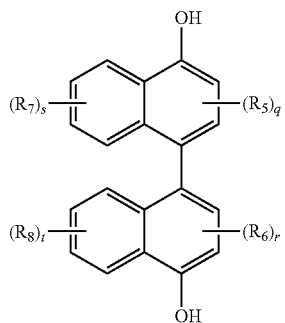

4

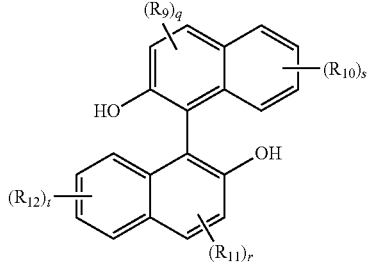

5 wherein
m, n, o, p are each independently 0, 1, 2, 3, or 4;
q and r are each independently 0, 1, or 2;
s and t are each independently 0, 1, 3, or 4;
$R_1$, $R_2$, $R_3$, $R_4$, $R_5$, $R_6$, $R_7$, $R_8$, $R_9$, $R_{10}$, $R_{11}$ and $R_{12}$ are each independently —H, —R', —NO$_2$, —NH$_2$, —N(R'R")$_2$, —N(R'R"R''')$_3{}^+$L$^-$, —CF$_3$, —CCl$_3$, —CN, —SO$_3$H, —PO$_3$H$_2$, —COOH, —CO$_2$R', —COR', —CHO, —OH, —OR', —O$^-$M$^+$, —SO$_3{}^-$M$^+$, —PO$_3{}^-$M$^+$, —COO$^-$M$^+$, —CF$_2$H, —CF$_2$R', —CFH$_3$, and —CFR'R" where R', R" and R''' are alkyl or aryl groups;
L is any negatively charged counter ion; and
M is any positively charged counter ion.

2. The flow battery of claim 1 wherein the second redox couple includes a second organic compound, the first organic compound having a standard electrode potential that is at least 0.3 volts higher than a standard electrode potential for the second organic compound.

3. The flow battery of claim 2 wherein the first organic compound has a standard electrode potential that is at least 0.1 V positive to a mercury/mercurous sulfate electrode (MSE) for the positive electrode electrolyte.

4. The flow battery of claim 3 wherein the second organic compound has a standard electron potential at least 0.1 V negative to the MSE for the negative electrode electrolyte.

5. The flow battery of claim 1 wherein the first organic compound has an acidity greater than the acidity of the ion exchange membrane.

6. The flow battery of claim 1 wherein $R_1$, $R_2$, $R_3$, $R_4$, $R_5$, $R_6$, $R_7$, $R_8$, $R_9$, $R_{10}$, $R_{11}$ and $R_{12}$ are each independently —H or $C_{1-6}$ alkyl.

7. The flow battery of claim 1 wherein $R_1$, $R_2$, $R_3$, $R_4$, $R_5$, $R_6$, $R_7$, $R_8$, $R_9$, $R_{10}$, $R_{11}$ and $R_{12}$ are each independently —H.

8. A flow battery comprising:
    a positive electrode;
    a positive electrode electrolyte including water and a first redox couple, the positive electrode electrolyte flowing over and contacting the positive electrode, the first redox couple including a first organic compound $Q^1$ and a reduction product $H_2Q_1$ of the first organic compound;
    a negative electrode;
    a negative electrode electrolyte including water and a second redox couple, the negative electrode electrolyte flowing over and contacting the positive electrode; and
    an ion exchange membrane interposed between the positive electrode and the negative electrode, wherein the first organic compound has formulae 6 or 7:

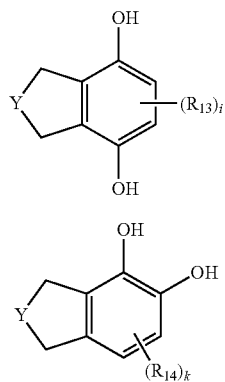

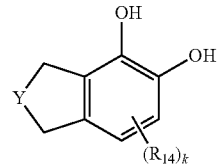

wherein i and k are each independently 0, 1, or 2;

$R_{13}$ and $R_{14}$ are each independently —H, —R', —$NO_2$, —$NH_2$, —N(R'R")$_2$, —N(R'R"R''')$_3^+$L$^-$, —$CF_3$, —$CCl_3$, —CN, —$SO_3H$, —$PO_3H_2$, —COOH, —$CO_2R'$, —COR', —CHO, —OH, —OR', —O$^-$M$^+$, —SO3$^-$M$^+$, —$PO_3^-$M$^+$, —COO$^-$M$^+$, —$CF_2H$, —$CF_2R'$, —CFH$^3$, and —CFR'R" where R', R" and R''' are alkyl or aryl groups;

Y is —(CH2)$_n$, —(CH2OCH2)$_n$, SO, $SO_2$, other substituted $C_{1-12}$ alkyl chains which may contain double bonds or triple bonds;

n is 1, 2, 3, 4, or 5;

L is a negatively charged counter ion; and

M is a positively charged counter ion.

9. The flow battery of claim 8 wherein the second redox couple includes a second organic compound, the first organic compound having a standard electrode potential that is at least 0.3 volts higher than a standard electrode potential for the second organic compound.

10. The flow battery of claim 9 wherein the first organic compound has a standard electrode potential that is at least 0.1 V positive to a mercury/mercurous sulfate electrode (MSE) for the positive electrode electrolyte.

11. The flow battery of claim 10 wherein the second organic compound has a standard electron potential at least 0.1 V negative to the MSE for the negative electrode electrolyte.

12. The flow battery of claim 10 wherein the first organic compound has an acidity greater than the acidity of the ion exchange membrane.

13. The flow battery of claim 10 wherein $R_{13}$ and $R_{14}$ are each independently —H or $C_{1-6}$ alkyl.

14. The flow battery of claim 10 wherein $R_{13}$ and $R_{14}$ are each independently —H.

15. A flow battery comprising:
a positive electrode;
a positive electrode electrolyte including water and a first redox couple, the positive electrode electrolyte flowing over and contacting the positive electrode, the first redox couple including a first organic compound $Q^1$ and a reduction product $H_2Q_1$ of the first organic compound;
a negative electrode;
a negative electrode electrolyte including water and a second redox couple, the negative electrode electrolyte flowing over and contacting the positive electrode; and
an ion exchange membrane interposed between the positive electrode and the negative electrode, wherein the first organic compound has formulae 8 and 9:

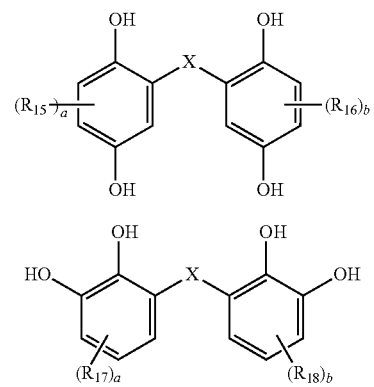

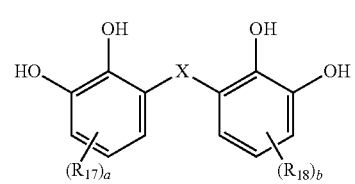

wherein a and b are each independently 0, 1, 2, or 3;

$R_{15}$, $R_{16}$, $R_{17}$ and $R_{18}$ are each independently —H, —R', —$NO_2$, —$NH_2$, —N(R'R")$_2$, —N(R'R"R''')$_3^+$L$^-$, —$CF_3$, —$CCl_3$, —CN, —$SO_3H$, —$PO_3H_2$, —COOH, —$CO_2R'$, —COR', —CHO, —OH, —OR', —O$^-$M$^+$, —SO3$^-$M$^+$, —PO3$^-$M$^+$, —COO$^-$M$^+$, —$CF_2H$, —$CF_2R'$, —CFH3, and —CFR'R" where R', R" and R''' are alkyl or aryl groups;

X is —(CH2)$_n$, —(CH2OCH2)$_n$, SO, $SO_2$, other substituted $C_{1-12}$ alkyl chains which may contain double bonds or triple bonds;

L is a negatively charged counter ion; and

M is a positively charged counter ion.

16. The flow battery of claim 15 wherein the second redox couple includes a second organic compound, the first organic compound having a standard electrode potential that is at least 0.3 volts higher than a standard electrode potential for the second organic compound.

17. The flow battery of claim 16 wherein the first organic compound has a standard electrode potential that is at least 0.1 V positive to a mercury/mercurous sulfate electrode (MSE) for the positive electrode electrolyte.

18. The flow battery of claim 17 wherein the second organic compound has a standard electron potential at least 0.1 V negative to the MSE for the negative electrode electrolyte.

19. The flow battery of claim 15 wherein the first organic compound has an acidity greater than the acidity of the ion exchange membrane.

20. The flow battery of claim 15 wherein $R_{15}$, $R_{16}$, $R_{17}$ and $R_{18}$ are each independently —H or $C_{1-6}$ alkyl.

21. The flow battery of claim 15 wherein $R_{15}$, $R_{16}$, $R_{17}$ and $R_{18}$ are each independently —H.

* * * * *

UNITED STATES PATENT AND TRADEMARK OFFICE
CERTIFICATE OF CORRECTION

| | |
|---|---|
| PATENT NO. | : 11,646,434 B2 |
| APPLICATION NO. | : 16/980549 |
| DATED | : May 9, 2023 |
| INVENTOR(S) | : Sri R. Narayan et al. |

It is certified that error appears in the above-identified patent and that said Letters Patent is hereby corrected as shown below:

In the Specification

Column 1, Line 19:
Insert:
--STATEMENT REGARDING FEDERALLY SPONSORED RESEARCH OR DEVELOPMENT
This invention was made with government support under DE-AR0000353 awarded by the U.S. Department of Energy. The government has certain rights in the invention.--

Signed and Sealed this
Twenty-fourth Day of October, 2023

*Katherine Kelly Vidal*

Katherine Kelly Vidal
*Director of the United States Patent and Trademark Office*